(12) United States Patent
Heaton et al.

(10) Patent No.: US 10,279,004 B2
(45) Date of Patent: *May 7, 2019

(54) METHODS AND COMPOSITIONS FOR ENHANCING OR MAINTAINING FERTILITY

(71) Applicant: Quality IP Holdings, LLC, Carson City, NV (US)

(72) Inventors: Amy L. Heaton, Salt Lake City, UT (US); Mitchell K. Friedlander, Salt Lake City, UT (US); Dennis Gay, Salt Lake City, UT (US)

(73) Assignee: Quality IP Holdings LLC, Salt Lake City, UT (US)

( * ) Notice: Subject to any disclaimer, the term of this patent is extended or adjusted under 35 U.S.C. 154(b) by 385 days.

This patent is subject to a terminal disclaimer.

(21) Appl. No.: 15/157,295

(22) Filed: May 17, 2016

(65) Prior Publication Data

US 2017/0333510 A1  Nov. 23, 2017

(51) Int. Cl.
A61K 36/00 (2006.01)
A61K 36/538 (2006.01)
A61K 31/198 (2006.01)
A23L 1/305 (2006.01)
A61K 9/14 (2006.01)
A61K 31/401 (2006.01)

(52) U.S. Cl.
CPC .......... A61K 36/538 (2013.01); A23L 1/3051 (2013.01); A61K 9/145 (2013.01); A61K 31/198 (2013.01); A61K 31/401 (2013.01)

(58) Field of Classification Search
CPC ...................................................... A61K 36/00
USPC ........................................................ 424/725
See application file for complete search history.

(56) References Cited

PUBLICATIONS

Homburg et al., Human Fertility, 2012; 15(4): 190-193.*

* cited by examiner

Primary Examiner — Michael V Meller
(74) Attorney, Agent, or Firm — Magleby Cataxinos & Greenwood

(57) ABSTRACT

Embodiments of the invention generally relate to methods and supplements for increasing, enhancing, or maintaining fertility in a human being.

1 Claim, 1 Drawing Sheet

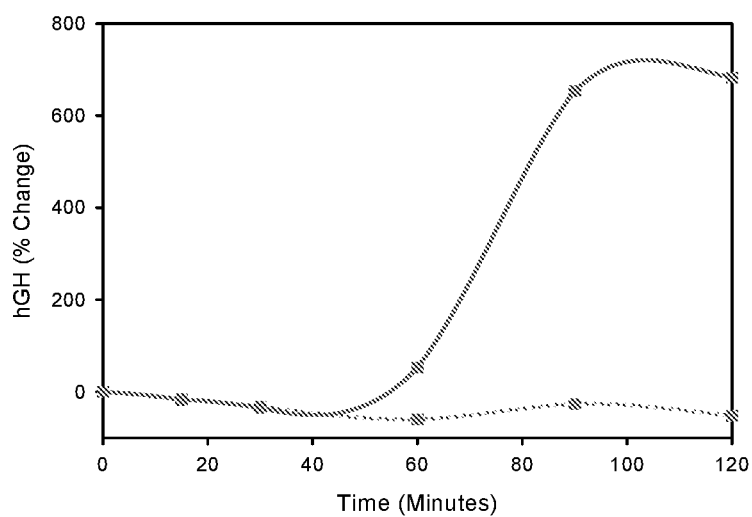

METHODS AND COMPOSITIONS FOR ENHANCING OR MAINTAINING FERTILITY

FIELD OF THE DISCLOSURE

The present disclosure generally relates to methods and supplements for improving fertility in a subject. In some embodiments, a nutritional supplement may be administered to a subject to increase levels of growth hormone (hGH) in the subject, thereby increasing fertility in the subject.

BACKGROUND

The primary biological function of human growth hormone (hGH) includes stimulating growth, cell repair, and regeneration. Once the primary growth period of adolescence concludes, the primary function of hGH in adulthood becomes that of cell regeneration and repair, helping regenerate skin, bones, heart, lungs, liver, and kidneys to their optimal, youthful cell levels. As is the case with many of our other hormones or their precursors, such as testosterone, estrogen, progesterone, DHEA, and melatonin, hGH levels decline with age. Therapeutically, many of these hormones can be replaced to offset some of the effects of aging such as menopausal symptoms in women or erectile dysfunction in men. Additionally, hGH and testosterone affect sterility and fertility in animals, including human beings.

The human body, like every other living entity, works on daily, or circadian, as well as monthly and annual rhythms. Daily growth hormone secretion diminishes with age with roughly half the levels at age 40 that we had when we were 20, and about one-third of those youthful levels at age 60. In some 60-year-olds, the levels are as low as 25% of the hGH levels in a 20-year-old. Symptoms of aging include loss of muscle, increase of fat, decreased physical mobility, decreased energy levels, and as a result, diminished socialization, diminished healing ability, and an increased risk of cardiovascular disease and decreased life expectancy. Low hGH levels are associated with the aging process and early onset of disease. For example, Rosen and Bengtsson noted an increased death rate from cardiovascular disease in hGH deficient patients. (Rosen, T., Bengtsson, B. A., Lancet 336 (1990): 285-2880)

Low hGH has been shown to decrease fertility in humans. See, e.g., Homburg, R., A. Singh, et al. (2012), "The re-growth of growth hormone in fertility treatment: a critical review." Hum Feral (Camb) 15(4): 190-193; Giampietro, A., D. Milardi, et al. (2009), "The effect of treatment with growth hormone on fertility outcome in eugonadal women with growth hormone deficiency: report of four cases and review of the literature." Feral Steril 91(3): 930 e937-911; Kalra, S., B. Kalra, et al. (2008), Growth hormone improves semen volume, sperm count and motility in men with idopathic normogonadotropic infertility. 10th European Congress of Endocrinology. Berlin, Germany, Endocrine Abstracts. 16: P613; Karaca, Z. and F. Kelestimur (2011), "Pregnancy and other pituitary disorders (including hGH deficiency)." Best Pract Res Clin Endocrinol Metab 25(6): 897-910; Magon, N., S. Singh, et al. (2011), "Growth hormone in male infertility." Indian J Endocrinol Metab 15 Suppl 3: S248-249; and Sakai, S., T. Wakasugi, et al. (2011), "Successful pregnancy and delivery in a patient with adult hGH deficiency: role of hGH replacement therapy." Endocr J 58(1): 65-68, the contents of each of which are incorporated herein by reference.

Until recently, hGH was available only in expensive injectable forms, and benefits from the restoration of hGH levels available only to those with the ability to pay. Most recently substances that can trigger the release of human growth hormone from an individual's own anterior pituitary gland have become available. These are generically referred to as secretagogues. Secretagogues have the ability to restore hGH levels, potentially to the levels found in youth. See, e.g., "Grow Young With hGH" by Dr. Ronald Klatz, President of the American Academy of Anti-Aging, published in 1997 by Harper Collins.

HGH-deficient adults have marked reductions in lean body mass, and within months of hGH treatment, gains in lean body mass, skin thickness, and muscle mass are observed. (Cuneo R C et al. J Appl Physiol 1991; 70:695-700; Cuneo R C et al. J Appl Physiol 1991; 70:688-694; Rudman D et al. N Engl J Med 1969; 280:1434-1438)

It is well-established that intravenous (IV) administration of some amino acids results in significant hGH secretion. Intravenous infusion of 183 mg of arginine/kg body weight in females increased hGH levels >20-fold, and 30 g of arginine elevated serum hGH levels 8.6 fold in males. (Merimee T J et al. N Engl J Med 1969; 280:1434-1438; Alba-Roth J et al. J Clin Endocrinol Metab 1988; 67:1186-1189) Other amino acids, such as methionine, phenylalanine, lysine, histidine, and ornithine, have also led to marked increases in hGH. (Alba-Roth, Muller, Schopohl, & von Werder, 1988; Chromiak & Antonio, 2002; Gourmelen, M., M. Donnadieu, et al. (1972) Ann Endocrinol (Paris) 33(5): 526-528)

Given the difficulties in IV administration of amino acids for widespread use, interest in elucidating the hGH response to oral amino acid supplements prompted testing of such supplements containing mainly arginine, lysine, and ornithine at varying amounts. Yet the pronounced variability in results among these studies makes clear the complexities involved in the design of an effective supplement for supporting hGH levels in the general public. (Suminski R R et al. Int J Sport Nutr 1997; 7:48-60; Lambert M I et al. Int J Sport Nutr 1993; 3:298-305; Corpas E et al. J Gerontol 1993; 48:M128-M133; Isidori A et al. Curr Med Res Opin 1981; 7:475-481; Fogelholm G M et al. Int J Sport Nutr 1993; 3:290-297; Chromiak J A, Antonio J. Nutrition 2002 July; 18(7-8):657-61)

Serum hGH levels differ in relation to various factors including age, gender, hormone status, and BMI. (Iranmanesh, Lizarralde, & Veldhuis, 1991); (Chowen, Frago, & Argente, 2004) Growth hormone has been shown to be important in multiple stages of pregnancy including early antral follicle recruitment, subsequent follicular growth, and oocyte maturation. Moreover, administration of growth hormone during the ovarian stimulation phase of in vitro fertilization (IVF) cycles has been shown to increase the probability of clinical pregnancy.

BRIEF SUMMARY OF THE DISCLOSURE

Described herein are nutritional supplements and methods for using the same. In embodiments, the nutritional supplement may be an amino acid secretagogue composition, which, when administered orally, stimulates the pituitary gland of a subject to release growth hormone (e.g., hGH), and results in the promotion or maintenance of fertility.

Some embodiments include an oral nutritional supplement that comprises, for example and without limitation: L-arginine, oxo-proline, L-lysine, and cysteine. Particular examples include an oral nutritional supplement that consists essentially of L-arginine hydrochloride, oxo-proline, L-lysine hydrochloride, N-acetyl-L-cysteine, L-glutamine, and schizonepeta powder.

Certain embodiments herein include an oral nutritional supplement dosage form that consists of 0.86 mmol L-arginine; 1.32 mmol oxo-proline; 2.05 mmol L-lysine; 1.53 µmol N-acetyl L-cysteine; 1.71 µmol L-glutamine; and 125 µg schizonepeta (aerial parts) powder. This oral nutritional supplement is referred to herein as "nutritional supplement." nutritional supplement may be orally administered in an amount of, for example, 2.9 grams (i.e., 4 unit dosage forms) to a human being, so as to stimulate the release of hGH and/or increase testosterone levels in the human being. The nutritional supplement may be administered on a regular basis, such as a weekly or monthly intake at a dosage tailored to the subject's needs; i.e., the nutritional supplement may be administered regularly as multiples (1×, 2×, etc.) of the structural units (pills, tablets, capsules, etc.) in accordance with the needs of the subject.

Some embodiments include a method for increasing growth hormone (e.g., hGH) and therefore increasing fertility in a subject (e.g., a human subject) that comprises administering (e.g., orally) a nutritional supplement to a subject to improve one or more objective health metrics, including for example and without limitation, increasing or enhancing pregnancy and live birth rate.

BRIEF DESCRIPTION OF THE FIGURES

FIG. 1 includes a plot of growth hormone levels measured in subjects after administration of an exemplary supplement compared to a placebo.

DETAILED DESCRIPTION

The determination of an effective and safe oral functional blend that stimulates hGH secretion in the general population is important, since athletes, entertainers, and now the general public seek effective hGH support supplements and understand hGH to have rejuvenating properties. Indeed, once partial to athletes and entertainers, the desire for effective supplements to provoke hGH increases now extends to the general public. Not only do they have a goal of building lean tissue and reducing fat, but also of improving/increasing fertility and providing other rejuvenating qualities that hGH is understood to provide. However, the literature on oral amino acids for use in stimulating hGH does not contain clear evidence for an optimized oral amino acid-containing blend able to stimulate hGH in the general public, including both men and women of a wide age range.

Therapeutic use of hGH has been used for improving pregnancy outcomes. Indeed, growth hormone has been shown to be important in multiple stages of pregnancy including early antral follicle recruitment, subsequent follicular growth, and oocyte maturation, and administration of growth hormone during the ovarian stimulation phase of in vitro fertilization (IVF) cycles has been shown to increase the probability of clinical pregnancy.

Embodiments herein provide a nutritional supplement for elevating growth hormone (e.g., hGH) and subsequently improving fertility, pregnancy, and live birth rate outcomes. Particular embodiments provide an amino acid-containing composition that is well tolerated, and may have the result of increasing or elevating hGH release in those individuals whose hGH release rates have slowed as a function of increasing age, or that have normal hGH levels but desire higher hGH levels. The compositions of the present disclosure also result in increasing or enhancing fertility. There is a need for a nutritional supplement that efficiently and demonstrably enhances the production and effects of natural human growth hormone and fertility outcomes in individuals of the general population.

Some embodiments herein provide a nutritional supplement for use by a human being. In particular embodiments, the nutritional supplement is an amino acid secretagogue composition, which, when administered orally, may stimulate the pituitary gland to produce hGH, and may jointly promote or maintain fertility.

Increased production of hGH may result in enhancement of fertility. In examples, a supplement herein may function as a dietary supplement by assisting the body's own ability to secrete hGH naturally, and in a manner which is safe and effective. Such a supplement may provide growth hormone therapy in a more affordable manner than existing compositions and methods, for example, injectable compositions.

Particular embodiments herein include an oral nutritional supplement that comprises L-lysine, L-arginine, oxo-proline, and one of cysteine and glutamine. In some examples, a supplement herein may comprise both cysteine and glutamine and/or schizonepeta powder. In particular examples, a functional dosage includes the L-arginine at a level between about 0.1-6 mmol and the oxo-proline between about 0.1-8 mmol, and/or the L-lysine in an amount between about 0.1-12 mmol. In particular examples, the cysteine and/or glutamine may be contained at a level between about 0.001-6 mmol.

Cysteine may be present in a supplement according to particular embodiments as n-acetyl L-cysteine, and the glutamine may be L-glutamine. Amino acids in a nutritional supplement herein may be delivered as non-toxic salts thereof, effective complexes thereof, stable chelates thereof, active esters thereof, functional derivatives thereof, and mixtures thereof which are effective to increase hGH levels in a subject from the general population.

Particular embodiments herein include an oral nutritional supplement that consists essentially of L-lysine (e.g., L-lysine HCl), L-arginine (e.g., L-arginine HCl), oxo-proline, N-acetyl-L-cysteine, L-glutamine, and schizonepeta (aerial parts) powder. In particular examples, a functional dosage includes L-arginine at a level between about 0.1-6 mmol and oxo-proline between about 0.1-8 mmol, and/or L-lysine in an amount between about 0.1-12 mmol. n-acetyl L-cysteine and/or L-glutamine may be comprised in some exemplary supplements at a level between about 0.001-6 mmol. In particular examples, a functional dosage includes L-arginine at a level between about 2.5-4.5 mmol and oxo-proline between about 4-6 mmol, and/or L-lysine in an amount between about 7-9 mmol. N-acetyl L-cysteine and/or L-glutamine may be comprised in some exemplary supplements at a level between about 0.001-0.5 mmol.

Certain embodiments herein include an oral nutritional supplement dosage form that consists of 0.86 mmol L-arginine; 1.32 mmol oxo-proline; 2.05 mmol L-lysine; 1.53 µmol N-acetyl L-cysteine; 1.71 µmol L-glutamine; and 125 µg schizonepeta (aerial parts) powder (nutritional supplement). Thus, an oral nutritional supplement dosage form may consist of 181.38 mg L-arginine HCl; 170.93 mg L-pyroglutamic acid; 374.83 mg L-lysine HCl; 0.25 mg N-acetyl L-cysteine USP; 0.25 mg L-glutamine; and 0.125 mg schizonepeta (aerial parts) powder, for example, in a capsule. In some examples, the oral nutritional supplement may be administered to a human being by orally administering four such dosage forms (i.e., 725.50 mg L-arginine HCl; 683.70 mg L-pyroglutamic acid; 1499.30 mg L-lysine HCl; 1.00 mg N-acetyl L-cysteine USP; 1.00 mg L-glutamine; and 0.50 mg schizonepeta (aerial parts) powder).

Some embodiments herein provide a method for increasing or enhancing fertility in humans, and increasing human growth hormone in humans that comprises orally administering a nutritional supplement for elevating growth hormone release to a healthy human being. As used herein, a "healthy human being" refers to a human being having any age-related decline in hGH, excluding any physiological deficiency that is not age related. Particular embodiments include oral administration of a nutritional supplement for elevating growth hormone release to a human that is at least 30 years old.

Other embodiments herein provide a method for increasing or enhancing fertility in humans, and increasing human growth hormone in humans that comprises orally administering a nutritional supplement for elevating growth hormone release to a human being that has a deficiency of hGH, or any condition resulting in low fertility or infertility, such as humans having pituitary disorders, idiopathic normogonadotropic infertility, and/or low hGH. In certain examples, oral administration of a nutritional supplement for elevating growth hormone release may improve fertility.

A nutritional supplement for elevating growth hormone release may be orally administered to a human being to improve health by affecting one or more condition(s) and/or disease(s) that depend upon androgen activity. Such conditions and diseases include, for example and without limitation: low fertility; infertility; and maintenance of fertility.

A nutritional supplement for increasing fertility and/or elevating growth hormone release may be used in combination with other hormone and/or steroid modulating supplements to enhance the effect of the nutritional supplements disclosed herein.

In accordance with the "consist essentially of" and "consisting essentially of" language herein, a nutritional supplement for elevating growth hormone release in some embodiments is essentially limited to the aforementioned ingredients, and does not include any additional active ingredients intended to add nutritional content (e.g., vitamins, minerals, etc.), but may include additional ingredients not intended to add nutritional content, for example, ingredients intended to fulfill a non-nutritional purpose (e.g., coloring, fillers, flavoring, an ingredient for maintaining the structural form, etc.).

Each ingredient of a nutritional supplement for increasing fertility and/or elevating growth hormone release may be prepared in accordance with any method known to one of ordinary skill in the art. Alternatively, each ingredient may be obtained in a fully prepared form from a commercially available source.

A nutritional supplement for increasing fertility and/or elevating growth hormone release may be in any suitable oral administration form, including but not limited to: a chewable form, a liquid form, a spray form, a capsule form, a suppository form, dissolvable wafer, and a powder form. In some embodiments, a dosage form of the nutritional supplement may be present in an amount of about 2.9 grams.

Irrespective of the structural form of the nutritional supplement for increasing fertility and/or elevating growth hormone release, the ingredients of the nutritional supplement may be distributed homogeneously or non-homogeneously within the nutritional supplement.

A nutritional supplement for increasing fertility and/or elevating growth hormone release may be ingested on a regular basis, such as a daily or weekly intake at a dosage tailored to an individual's needs, i.e., the nutritional supplement is to be taken regularly as multiples (1×, 2×, etc.) of the dosage form (e.g., pills, tablets, capsules, etc.) in accordance with the needs of the individual. For example, a senior citizen leading a sedentary life is likely to need higher daily doses than does a young person engaged in regular strenuous exercise (e.g., a weight lifter).

Alternatively, the nutritional supplement for increasing fertility and/or elevating growth hormone release may be ingested on an as-needed basis at a dosage tailored to the individual's needs. Medical or nutritional counseling may be beneficial for arriving at a desirable or optimal dosage tailored to the individual's needs. The nutritional supplement may be administered, for example, from one to three times daily, or, by way of further example, the supplement may be administered every other day or once a week. In particular embodiments, the nutritional supplement may be administered on an empty stomach.

In certain embodiments, a nutritional supplement for increasing fertility and/or elevating growth hormone release comprises a particular combination of types of amino acids, mass ranges, and specific formulations that have been selected to be synergistically balanced and of adequate quantity to achieve a desired physiological effect, e.g., growth hormone release and increased fertility. Improper combinations of the same amino acids may be ineffective. The component amino acids may be synergistic in the sense that several of them, when combined together, synergistically stimulate the release of human growth hormone, leading to enhanced fertility. The combination of amino acids in particular embodiments was also chosen to reduce or inhibit chemical combination or reaction between the component amino acids.

EXAMPLES

Example 1: Effect of an Oral Nutritional Supplement Single Dose on hGH Levels

The short-term effects of a single oral nutritional supplement on hGH levels 2 hours post ingestion was studied in 16 healthy subjects [12 males, four females; nine Caucasian, six African American, one other; mean age=32±14 years; body mass index=26.4±5.0 ranging from 19.1 to 36.8 kg/m$^2$]. Each subject reported to the Inpatient Unit on two occasions one week apart. After an overnight fast, subjects had an IV line placed and baseline bloods samples were drawn at −30, −15, and 0 minutes.

Subjects were then asked to swallow the capsules of supplement (nutritional supplement) or an identical looking placebo. nutritional supplement is a 2.9 g/dose blend of L-lysine HCl, L-arginine HCL, oxo-proline, N-acetyl-L-cysteine, L-glutamine, and schizonepeta (aerial parts) powder. Blood was drawn at 15, 30, 60, 90, and 120 minutes for assay. Human GH was measured at each time point using the Siemens Immulite™ 2000 (intra-assay CV was 3.72%, inter-assay CV was 5.70%, and the detection limit for hGH was 0.05 ng/mL. The −15 and 120 minute time points were additionally assayed for triiodothyronine (T3) as informative for mechanistic investigations.

The mean growth hormone increased 682% after the supplement from 0.17 at baseline to 1.33 ng/mL at 120 minutes, compared to a mean decrease of 52% after the placebo from 0.93 to 0.45 ng/mL. FIG. 1.

The mean change in hGH levels from baseline to 120 minutes (hGH at 120 minutes minus hGH at 0 minutes), was 1.15 (95% CI: 0.17, 2.14) ng/mL after the supplement, versus −0.48 (−1.47, 0.50) ng/mL after the placebo, demonstrating a statistically significant differential effect (P=0.01). After the supplement, the mean AUC for hGH across 120 minutes was 20.43 (95% CI: 19.90, 20.95) ng/mL/min which was significantly higher (P=0.04) than placebo at 19.67 (18.74, 20.59) ng/mL/min. Overall, 120 minutes after taking the supplement, hGH levels were significantly higher in absolute levels or by AUC.

As daily circadian levels of T3 naturally decrease during the morning hours, at which the current trial was scheduled, it was not surprising that placebo levels between the −15 and 120 minute time points decreased by −6.10 ng/dL (106 to 100 ng/dL, P=0.01). In contrast, the nutritional supplement group exhibited a deceased reduction in T3 by nearly one-half over the same time course, −3.3 ng/dL (101-97.3 ng/dL, NS), which was not a significant reduction compared to baseline, as was the reduction in the placebo group. These results affirm that somatostatin inhibition plays a mechanistic role in the ability of nutritional supplement to induce significant increases in serum hGH levels in human subjects.

At 120 minutes, hGH concentrations were two-fold higher in women (2.3±1.1 ng/mL, n=4) than in men (1.0±0.4 ng/mL, n=12, although the study was not adequately powered for these comparisons. Nevertheless, these findings support an enhanced effect of the nutritional supplement supplement in women.

An eight-fold increase was observed, equivalent to 682%, in hGH levels 120 minutes after a single oral supplement of nutritional supplement. The study had a broad range of ages and BMIs and included both genders. An additional advantage of the present study over previous hGH evaluations is that it contained a placebo control group and was randomized and double-blinded.

These findings demonstrate that a specialized low-dose amino acid supplement can significantly increase short-term hGH levels. Future studies will examine whether such increases in hGH with oral amino acid supplementation increase fat-free mass and strength. This indeed may be the case, since elderly subjects administered oral hGH secretagogues for six and 12 months have sustained increases in lean body mass and improved physical function.

The absolute magnitudes of these results are somewhat difficult to directly correlate among past studies, as commercial hGH assays use different antibodies to target specific hGH epitopes. Therefore, different antibodies and assays are less likely to recognize some specific isoforms and fragments of the hGH molecule. This results in variability of the normal range of the hGH measurements in different assays. Indeed, the same hGH sample measured using different assays can vary two- to three-fold, limiting the ability to compare actual hGH levels across studies. Nevertheless, the mean levels of hGH reached after the subcutaneous injection of 0.06 IU of hGH in the treatment of hGH deficient subjects was 0.4 ng/mL, a value that was clearly in the range of values seen in our study with oral amino acids.

Findings obtained from a randomized, blinded, placebo-controlled study strengthen the evidence that oral administration of amino acids, when compounded properly, can increase hGH serum levels, wherein nutritional supplement administration showed an eight-fold increase, equivalent to a 682% increase in hGH levels, 120 minutes after a single oral dose. In addition, we elucidate some mechanistic details for these significant hGH increases as through somatostatin inhibition, supported by our results on the 120 minute results on T3 levels in the same subjects.

Example 2: Effect of an Oral Nutritional Supplement on Fertility

The effects of an oral nutritional supplement on fertility were studied in a group of healthy human subjects. Subjects were asked to swallow capsules of nutritional supplement.

Case 1:

A 27-year-old woman was admitted to St. Mark's Center for Women's Health for a physical examination with complaints of irregular menses and secondary infertility. Six years previously, she had given birth to her first child. The pregnancy was uneventful with spontaneous labor at 38 weeks. She underwent cesarean section for delivery after failure to progress in labor, and gave birth to a healthy baby. The subject was unable to breastfeed because she did not have sufficient milk production.

Following the birth of her first child, she had experienced weight gain and difficulty losing weight. Her menstrual periods were light and infrequent, numbering approximately two per year with each lasting approximately three days. She and her partner failed to conceive a pregnancy over a six-year period while actively attempting to get pregnant for the last four years.

Upon examination, clinical results were consistent with Polycystic Ovary Syndrome (PCOS), and a uterine ultrasound was performed. Ultrasound confirmed polycystic ovaries and PCOS diagnosis. The patient elected a conservative mode of management by engaging in a targeted diet and exercise program for weight loss. However, she was only able to lose a marginal amount of weight and experienced no changes in menstrual cycles.

After approximately a year and a half of attempting weight loss as the only mode of management, the subject started daily supplementation with nutritional supplement (2.9 g/day). After the first two months of nutritional supplement intake, she had a menstrual period. After one more month of supplementation, she had another menstrual period. After one more month of supplementation for a total of four months of supplementation, she confirmed pregnancy. She discontinued nutritional supplement supplementation after pregnancy was confirmed.

Her second pregnancy proceeded to term without complications and the patient gave birth to a healthy baby boy weighing 10 lbs 6 oz, length 21½ inches.

Case 2:

A 33-year-old woman, BMI 37.2, was referred to a reproductive center on Aug. 15, 2013 for secondary infertility and recurrent pregnancy loss. Medical impression included SAB×2 (1 with prior partner); SVD×1; ovulatory dysfunction; menses every 2-3 months; moderate dysmenorrhea; minimal endometriosis. [Male factors showed normal semen analysis].

History: In May of 2001 she experienced an SAB (miscarriage). In January of 2009, she gave birth to a healthy daughter (preeclampsia, on bedrest from 29 weeks), having conceived after a second cycle of Clomid. In January of 2012, she experienced a second SAB (bleeding×2 weeks, serum HCG low and then went down, no sac seen on ultrasound, biochemical).

In August of 2013, the patient had her initial consult and initiated treatment:

Ovulation Induction (OI), Anovulation

The patient presented with the following test results and treatment:

28 Aug. 2013 Baseline US showed 19 total antral follicle counts (AFC), 4 mm endometrial thickness, 1.5 cm leiomyoma in anterior wall of fundus noted 28 Aug. 2013 E2<25, antimullerian hormone (AMR) 0.8, follicle stimulating hormone (FSH) 2.4, Prolactin 16.4, HgbA1c 5.5%, TSH 1.2

Femara 5 mg days 3-7

13 Sep. 2013 P4 (progesterone) 0.2, day 23

Provera 10 mg×10 days

Intrauterine Insemination (UI), Conceived

The patient presented with the following test results and treatment:

21 Nov. 2013 Menses

Femara 7.5 mg days 3-7

Took nutritional supplement daily from 29 Nov. 2013 to 6 Jan. 2014

5 Dec. 2013 ultrasound on day 14 showed 15 total AFC, lead follicle measuring 23 mm on the right, 7.5 mm endometrial thickness Human chorionic gonadotropin (HCG) 10 k 7 Dec. 2013 IUI on cycle day 15. Semen sample showed 4.7 ml, 109 mill/ml, 67% motility, 343.2 mill total motile sperm count (TMC), 2.5 progression preprep 21.9 mill TMC inseminated after gradient preparation 30 Dec. 2013 HCG 5921

2 Jan. 2014 ultrasound showed single IUP measuring 5 weeks 6 days, FHT 114

Case 3:

A 29-year-old woman, 156 cm tall, weighing 49.9 kg (BMI 20.5 kg/m2) desired a pregnancy but had been impacted by endometriosis symptomology since adolescence. She declined surgical and hormonal interventions since her initial diagnosis and managed symptoms of menorrhagia and dysmenorrhea through nutritional and active-lifestyle approaches.

After six months of unprotected intercourse, the subject conceived. She gained 29 kg over the course of pregnancy and suffered from mild nausea, occasional vomiting, and persistent colds. She otherwise had a non-eventful pregnancy and underwent a planned cesarean section for breach presentation at 39 weeks. After delivery, the subject was able to breastfeed for several weeks, after which she did not have sufficient milk production to continue breastfeeding. The subject experienced sharp abdominal pains with any physical motion at the site of cesarean section incision for several months after the delivery and was unable to exercise until the pain subsided. The subject also experienced symptoms of postpartum depression.

Four months following the delivery, the subject began daily supplementation with nutritional supplement (2.9 mg/day) and engaged in fitness training. She lost 25 kg and competed in a competitive running event. Nine months after beginning daily supplementation with nutritional supplement, the subject conceived an unplanned, second pregnancy from a single unprotected event. She discontinued nutritional supplement supplementation after pregnancy was confirmed.

The subject suffered from increased symptoms of illness compared to her first pregnancy including nausea, vomiting on 12 occasions, and persistent colds, but had no other complications. She underwent a planned cesarean section at 42 weeks after spontaneous labor was not reached. The subject breastfed her baby for a period of two weeks. She initiated daily nutritional supplement supplementation four weeks after the delivery and two weeks after ceasing breastfeeding.

Three months after restarting daily supplementation with nutritional supplement, the subject completed a half-marathon. One month later and four months after restarting nutritional supplement, the subject conceived an unplanned, third pregnancy, once again from a single unprotected event. The subject continued nutritional supplement supplementation throughout the pregnancy and did not experience symptoms of illness as she did with her previous pregnancies. She underwent a planned cesarean section and tubal ligation at 39 weeks, giving birth to her third healthy baby.

As no other observable changes in diet or medication took place, nutritional supplement appears to have heightened her fertility, leading to her timely second and third improbable pregnancies. Ingestion of nutritional supplement also appears to have reduced postpartum depressive symptoms after her second and third deliveries, as well as eliminating physical illness symptoms during her third pregnancy. She notes that she did not experience pain with physical motion at the incision site after her second and third cesarean sections as she did with her first, despite the short succession between multiple surgeries.

While embodiments of the present invention have been described herein for purposes of illustration, many modifications and changes will become apparent to those skilled in the art. Accordingly, the appended claims are intended to encompass all such modifications and changes as fall within the true spirit and scope of this invention.

We claim:

1. A method for treating humans with fertility problems consisting essentially of orally administering to the humans with fertility problems an oral nutritional supplement unit dosage form consisting essentially of therapeutically effective amounts of L-arginine, oxo-proline, L-lysine, N-acetyl L-cysteine, L-glutamine, and aerial parts of schizonepeta.

* * * * *